US012029596B2

(12) United States Patent
Shastri et al.

(10) Patent No.: US 12,029,596 B2
(45) Date of Patent: Jul. 9, 2024

(54) MOBILITY OF AN X-RAY IMAGING SYSTEM

(71) Applicant: KONINKLIJKE PHILIPS N.V., Eindhoven (NL)

(72) Inventors: Suyash Shastri, Pune (IN); Jacob De Boer, Best (NL); Bhushan Shripad Barve, Pune (IN); Sujata Bhalerao, Pune (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 284 days.

(21) Appl. No.: 17/607,058

(22) PCT Filed: Apr. 29, 2020

(86) PCT No.: PCT/EP2020/061856
§ 371 (c)(1),
(2) Date: Oct. 28, 2021

(87) PCT Pub. No.: WO2020/221793
PCT Pub. Date: Nov. 5, 2020

(65) Prior Publication Data
US 2022/0151577 A1 May 19, 2022

(30) Foreign Application Priority Data
May 2, 2019 (EP) .................................... 19172171

(51) Int. Cl.
*A61B 6/00* (2024.01)
(52) U.S. Cl.
CPC .......... *A61B 6/4405* (2013.01); *A61B 6/4441* (2013.01); *A61B 6/4452* (2013.01); *A61B 6/4476* (2013.01)

(58) Field of Classification Search
CPC ... A61B 6/4405; A61B 6/4441; A61B 6/4452; A61B 6/4476; A61B 6/548;
(Continued)

(56) References Cited

U.S. PATENT DOCUMENTS 5,503,416 A 4/1996 Aoki
6,374,937 B1 4/2002 Galando
(Continued)

FOREIGN PATENT DOCUMENTS

JP 2017000486 A 1/2017
WO 2016153425 A1 9/2016

OTHER PUBLICATIONS

International Search Report and Written Opinion of PCT/EP2020061856 dated Jul. 31, 2020.

*Primary Examiner* — Irakli Kiknadze (57) ABSTRACT

A base for a mobile X-ray imaging system comprises a carriage, a mounting structure mounted to the carriage and that movably holds an imaging device, a wheel base, and a controller. The wheel base comprises at least three wheels mounted to the carriage to be pivotable around a vertical pivot axis and to rotate around a horizontal wheel axis. At least two of the wheels form rearside wheels and at least one of the wheels forms a frontside wheel. Each rearside wheel is independently steerable in its orientation around the vertical pivot axis by a pivot actuator. Each rearside wheel is independently drivable around its horizontal wheel axis by a drive actuator to move the base relative to the floor. The controller steers and drives the rearside wheels.

19 Claims, 8 Drawing Sheets

(58) Field of Classification Search
CPC ....... A61B 6/4464; A61B 6/56; A61B 6/0407;
A61B 6/105; A61B 6/467; A61B 6/4417;
A61B 6/487; A61B 5/055; A61B 6/4488;
A61B 6/035; A61B 6/027; A61B 6/4014;
A61B 6/4021; A61B 6/54; A61B 6/4411;
A61B 6/4447; A61B 6/547; A61B 6/032;
A61B 6/4085; A61B 6/485; A61B 6/00;
A61B 6/10; A61B 6/4429; A61B 6/4423;
G01T 1/1606; G01R 33/4812; H02G
11/006; B60B 33/0055; B60B 33/0005;
B60B 33/0039; B60B 33/028; B60B
33/0068; B60B 33/0073; B60B 33/0049;
B60B 33/0015; B62D 7/02; B62D 11/04

USPC ..................................... 378/42, 62, 102, 198
See application file for complete search history.

(56) References Cited

U.S. PATENT DOCUMENTS

| | | | |
|---|---|---|---|
| 6,814,490 | B1 | 11/2004 | Suhm |
| 8,657,494 | B2* | 2/2014 | Muller ................... A61B 6/547 |
| | | | 74/25 |
| 10,070,833 | B2 | 9/2018 | Shirota |
| 10,136,866 | B2 | 11/2018 | Onobori |
| 10,151,710 | B2* | 12/2018 | Pellechia ............. G01N 23/083 |
| 2008/0123818 | A1 | 5/2008 | Alder |
| 2012/0128130 | A1 | 5/2012 | Boomgaarden |
| 2012/0219122 | A1 | 8/2012 | Herrmann |
| 2015/0085992 | A1 | 3/2015 | Grady |
| 2017/0215826 | A1 | 8/2017 | Johnson |
| 2018/0279980 | A1* | 10/2018 | Barker ................. A61B 6/4458 |
| 2018/0279981 | A1 | 10/2018 | Fehre |
| 2019/0029619 | A1 | 1/2019 | Ogura |
| 2019/0069864 | A1* | 3/2019 | Tkaczyk ................ A61B 6/025 |
| 2019/0150865 | A1* | 5/2019 | Johnson ............... A61B 6/4441 |
| 2020/0170608 | A1* | 6/2020 | Makino ................ A61B 6/4405 |
| 2021/0177371 | A1* | 6/2021 | Wang .................... A61B 90/39 |
| 2021/0401382 | A1* | 12/2021 | Roberts ................. A61B 6/464 |

* cited by examiner

MOBILITY OF AN X-RAY IMAGING SYSTEM

CROSS-REFERENCE TO PRIOR APPLICATIONS

This application is the U.S. National Phase application under 35 U.S.C. § 371 of International Application No. PCT/EP2019/078739, filed on Oct. 22, 2019, which claims the benefit of European Patent Application No. 18202469.5, filed on Oct. 25, 2018 and European Patent Application No. 19164249.5, filed on Mar. 21, 2019. These applications are hereby incorporated by reference herein.

FIELD OF THE INVENTION

The present invention relates to the mobility of an X-ray imaging system, and relates in particular to a base for a mobile X-ray imaging system, to a mobile X-ray imaging system and to a method for moving a base of a mobile X-ray imaging system.

BACKGROUND OF THE INVENTION

As an example, mobile X-ray systems are used for acquisition of X-ray images, e.g. in crowded operating areas where limited space is available to position and maneuver the system. It may be required to make different rotations in combination with linear movements with the complete system in the operating area, for instance with stitching technology (stitching X-ray images), a larger movement range is required along the patient lying on the patient table. Mobile X-ray systems are used with wheels on their base so that they can be moved within the operational room.

As an example, US 2019/029619 A1 describes a mobile radiation generation apparatus which prevents the unsteady motion of a carriage unit with a simple structure and provides the fine adjustment of the position of a radiation-emitting unit. Each of a front wheel and a rear wheel of a carriage unit is a caster that swivels about a swivel axis extending in a vertical direction. A support that vertically stands on the carriage unit supports a base end of an arm unit having a free end to which an X-ray emitting unit is attached. The arm unit rotates about a rotation axis parallel to the swivel axis with respect to the carriage unit. The carriage unit includes a front pedal that is provided closer to the front wheel than the support and is used to lock both the rotation and swivel of the caster at the same time.

As an example, US 2012/0219122 A1 describes a wheeled C-arm support device for a mobile C-arm X-ray machine and an associated method for swiveling the C-arm support device. The C-arm support device includes two steerable front wheels, two freely movable rear wheels and a steering unit that may steer the two steerable front wheels simultaneously inward by the same angle. A line of intersection of surfaces formed by outer sides of the two steerable front wheels form an imaginary swivel axis of the C-arm support device.

However, it has been shown that moving of mobile X-ray systems e.g. in an operational room can be cumbersome.

SUMMARY OF THE INVENTION

There may thus be a need to provide X-ray imaging systems with improved mobility.

The object of the present invention is solved by the subject matter of the independent claims; further embodiments are incorporated in the dependent claims. It should be noted that the following described aspects of the invention apply also for the base for a mobile X-ray imaging system, for the mobile X-ray imaging system and for the method for moving a base of a mobile X-ray imaging system.

According to the present invention, a base for a mobile X-ray imaging system is provided. The base comprises a carriage, a mounting structure mounted to the carriage, a wheelbase with a wheel arrangement of at least three wheels mounted to the carriage and a wheel controller. The mounting structure is configured to movably hold an X-ray imaging device. The carriage comprises a first end portion and an opposite second end portion. The first end portion is configured as a front end arrangeable closer to an object during X-ray imaging, and the second end portion is configured as a rear end arrangeable away from an object during X-ray imaging. The first end portion and the opposite second end portion are arranged along a longitudinal center line of the base. The at least three wheels are each mounted to the carriage to be pivotable around a vertical pivot axis and to rotate around a horizontal wheel axis. At least two of the at least three wheels are forming rearside wheels mounted in the region of the rear end; and at least one of the at least three wheels is forming a frontside wheel mounted in the region of the front end. At least two of the rearside wheels are independently actively steerable in their orientation around the vertical pivot axis by a pivot actuator. Further, the at least two of the rearside wheels are configured to be each independently actively drivable around their horizontal axis by a drive actuator to move the mobile base in relation to a floor. The wheel controller is configured to actively steer and drive at least the at least two of the rearside wheels such that the base rotates around a virtual point of rotation that is aligned with the longitudinal center line of the base.

According to an example, a base for a mobile X-ray imaging system is provided. The base comprises a carriage, a mounting structure mounted to the carriage and a wheelbase with a wheel arrangement of at least three wheels mounted to the carriage. The mounting structure is configured to movably hold an X-ray imaging device. The carriage comprises a first end portion and an opposite second end portion. The first end portion is configured as a front end arrangeable closer to an object during X-ray imaging, and the second end portion is configured as a rear end arrangeable away from an object during X-ray imaging. The at least three wheels are each mounted to the carriage to be pivotable around a vertical pivot axis and to rotate around a horizontal wheel axis. At least two of the at least three wheels are forming rearside wheels mounted in the region of the rear end; and at least one of the at least three wheels is forming a frontside wheel mounted in the region of the front end. The rearside wheels are independently actively steerable in their orientation around the vertical pivot axis by a pivot actuator. Further, at least one of the wheels is actively drivable around its horizontal axis by a drive actuator to move the mobile base in relation to a floor.

This provides an improved mobility due to the active control of the actively driven wheels which results in a facilitated and precise movement of the base, e.g. for an X-ray imaging system.

In an example, both wheels are steerable with one actuator. For example, a transmission between both wheels is provided, e.g. a chain, timing belt or cable. For rotation or parallel base movement, the transmission may be provided to be contrary or synchronized around the vertical pivot axis.

In a further example, two or more of the wheels are actively drivable around their respective horizontal axis.

This may be provided by a drive actuator. A transmission may be provided to allow individual movement control of the wheels, or two or more actuators can be provided to allow individual movement control of the wheels. According to an example, at least one of the rearside wheels is configured to be drivable by the drive actuator.

According to an example, at least two of the rearside wheels are configured to be each independently drivable by the drive actuator.

As a result, the rearside wheels, which can be mounted with a greater distance between them, provide an improved leverage in terms of achieving the movement of the base. According to an example, the rearside wheels are each independently actively steerable such that the horizontal wheel axes of the rearside wheels intersect at a cross point; wherein the cross point forms a virtual point of rotation of the mobile base.

As a result, the base can rotate within the horizontal plane. The defined cross point can be defined in relation with further geometrical points of the imaging system, i.e. the imaging chain.

According to the present invention, also a mobile X-ray imaging system is provided. The system comprises a base according to one of the preceding examples and an X-ray imaging device with an X-ray source and an X-ray detector. The X-ray imaging device further comprises a support structure. At least the X-ray source is mounted to the support structure. Further, the support structure is movably mounted to the mounting structure of the base.

According to an example, the support structure comprises a C-arm; the X-ray source and the X-ray detector are mounted to opposite ends of the C-arm. The C-arm is slidably hold by a sleeve-like mount, which is rotatable around a horizontal axis of rotation. The horizontal axis of rotation and a centerline between the X-ray source and the X-ray detector are crossing each other at a point of intersection. Further, the sleeve-like mount is rotatable around a vertical axis of rotation.

According to an example, the virtual point of rotation of the mobile base and the point of intersection are alignable in a vertical manner.

According to an example, the virtual point of rotation of the mobile base and the vertical axis of rotation are alignable in a vertical manner.

According to the present invention, also a method for moving a base of a mobile X-ray imaging system is provided. The method comprises the following steps:
  a) independently actively steering rearside wheels of a wheel arrangement of at least three wheels mounted to the carriage in their orientation around a vertical pivot axis by a pivot actuator; wherein the wheels are each mounted to the carriage to be pivotable around a vertical pivot axis; and
  b) actively driving at least one of the wheels by a drive actuator to move the mobile base in relation to a floor; wherein the at least three wheels are each mounted to the carriage to rotate around a horizontal wheel axis.

The wheels are mounted to a carriage to which a mounting structure is mounted, which mounting structure is configured to movably hold an X-ray imaging device. The carriage comprises a first end portion and an opposite second end portion. The first end portion is configured as a front end arrangeable closer to an object during X-ray imaging, and the second end portion is configured as a rear end arrangeable away from an object during X-ray imaging. At least two of the at least three wheels are forming rearside wheels mounted in the region of the rear end; and at least one of the at least three wheels is forming a frontside wheel mounted in the region of the front end.

According to an aspect, a solution is realized where two wheels can achieve an angled orientation with respect to each other and the cross point of both wheel center lines will create a rotation point around which the complete system will rotate. This cross/rotation point can be for instance in the center of the image chain for image rotation, or in the center of the C-arm panning rotation useful for stitching or park position. In this case the C-arm panning rotation range is enlarged, since the over-balancing (or tipping over) problem is reduced by the possibility to move the base with its wheels below the C-arm. With the new solution, the center of gravity will remain in the same horizontal centerline. This can be beneficial to make the system even smaller (e.g. decreasing the distance between the backside wheels) and also more cost effective, since a C-arm panning rotation module mounted on top of the height positioning module can be eliminated. The wheel centerline cross point can also be orientated further backwards in x-direction to create panning rotations with less x-displacement, which is the result of a larger rotation radius. In an example, the base is used for mobile X-ray systems, and in particular for X-ray image stitching, X-ray image rotation, and automatic position control. The base can be used in X-ray diagnostic and treatment systems for mobile applications.

For a single-user concept, wheel rotation and orientation are motorized, which also fits with improving sterility in the way of working e.g. in the operational room.

Further, combinations are provided between completely motorized positioning and completely manual positioning. Further, also motorized floor movements with manual wheel orientation are provided in an example; e.g. wheel orientation can be done with steering handles.

With different back wheel orientations of a mobile surgery system on the floor, different movement directions can be realized. These wheel orientations can also be orientated in different angles which makes it possible to realize multiple rotation points.

These multiple rotation points make it possible to rotate the complete mobile imaging system, for instance around the image chain or around the current C-arm panning rotation. For other use cases these wheels can also be orientated/positioned parallel to each other so the complete system can move in x- and y-direction, or combinations of the x- and y-directions. The wheel rotation and wheel orientation can also be motorized; also, manual movements can be executed or a combination of motorized and manual movements like motorized wheel rotations on the floor and wheel orientation done with manual steering handles.

The solution aims to improve several points of usage for multiple applications, e.g. to create multiple rotation points, which make it possible to rotate the complete system on the floor around multiple cross/rotation points; to provide larger C-arm panning range above e.g. ±10°; while linear movements still possible in x-y or combined directions. In combination with motorized rotation movements, the floor movements are motorized and also the wheel orientations are motorized. This also supports the single-user concept where e.g. a doctor has full control over all movements of the system. It's also possible to combine this with controlled positions; e.g. automatic position control is provided which makes it possible to move with the system between stored positions. It's also possible to combine this with scanning movements, rotations and linear movements. Movements can be executed parallel to the patient table, perpendicular or combinations of these.

The provided rotation schemes due to the particular configuration of the base are suitable for imaged guided therapy mobile C-arm systems like mobile C-arm systems.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list. The term "subject" may also be referred to as individual. The "subject" may further also be referred to as patient, although it is noted that this term does not indicate whether any illness or disease is actually present with the subject.

Figure 1A:
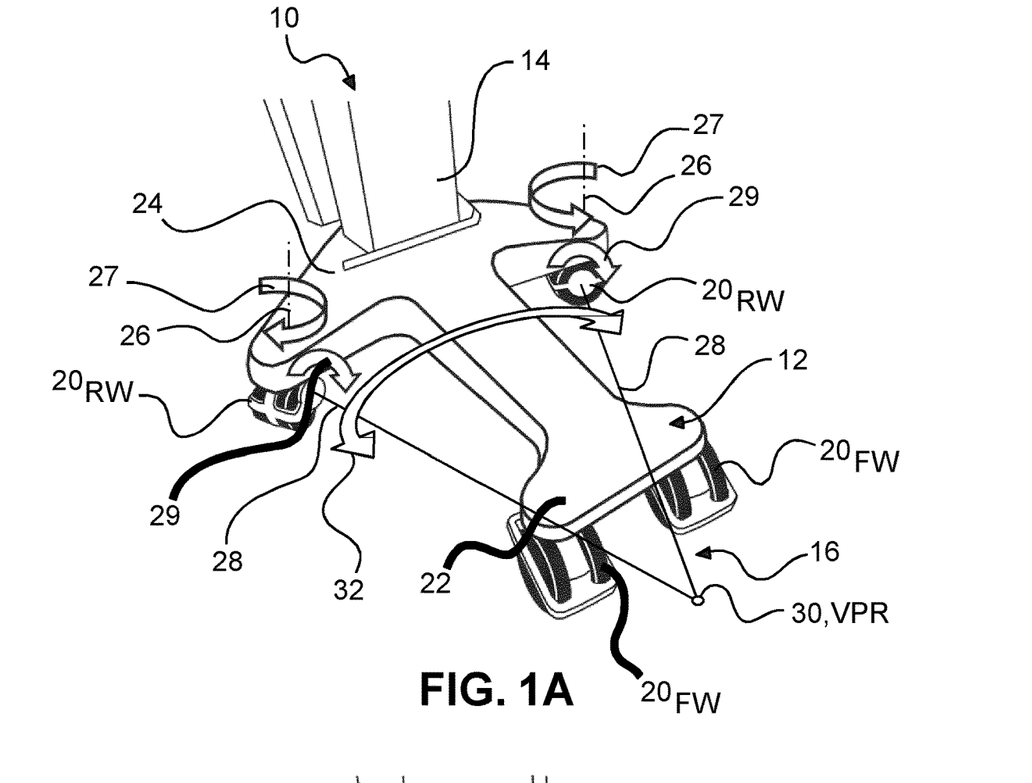
FIGS. 1a and 1b show an example of a base with a first wheel arrangement in two perspective views.
Figure 1B:
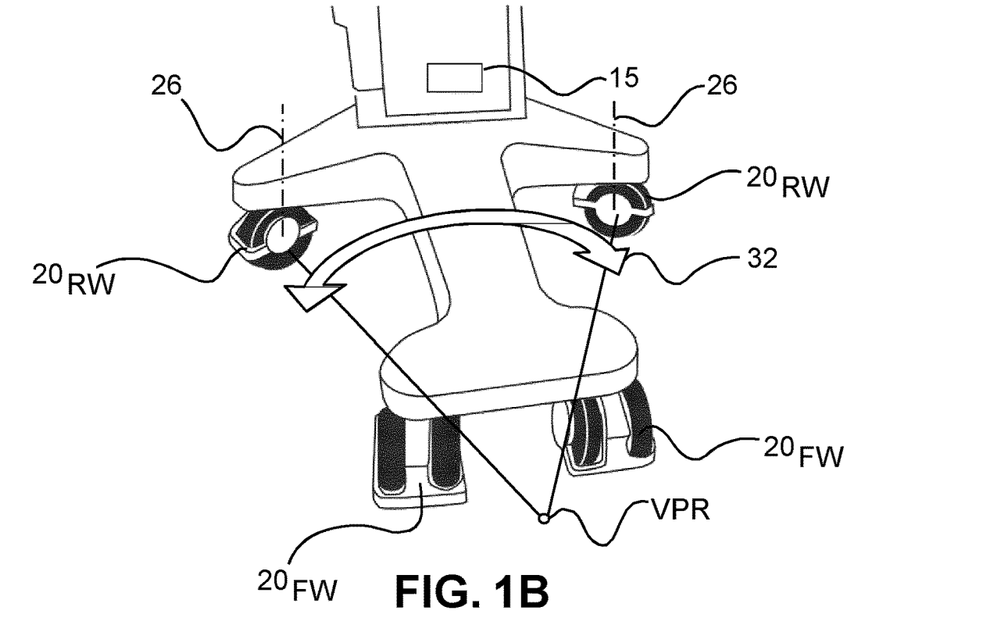

FIGS. 1a and 1b show an example of a base 10 for a mobile X-ray imaging system. The base 10 comprises a carriage 12, a mounting structure 14 mounted to the carriage and a wheel base 16 with a wheel arrangement of at least three wheels 20 mounted to the carriage and a wheel controller 15. It is noted that the wheel controller 15 is not shown in some of the figures, but provided according to some examples. The mounting structure 14 is configured to movably hold an X-ray imaging device (see also below, FIG. 4). The carriage 12 comprises a first end portion 22 and an opposite second end portion 24. The first end portion 22 is configured as a front end arrangeable closer to an object during X-ray imaging, and the second end portion 24 is configured as a rear end arrangeable away from an object during X-ray imaging (see also below, FIG. 4). The first end portion 22 and the opposite second end portion 24 are arranged along a longitudinal center line 17 of the base (see FIG. 2B). It is noted that the center line 17 is shown only in a few of the figures, but provided in the others, too.

It is noted that the drawings shown an example with double wheels, i.e. two wheel elements, for each of the rearside and frontside wheels. In a further example, a single-wheel design is provided as an option. A further option provides a combination of single wheels, for example for the rearside wheels or the frontside wheels, and double wheels, for example for the frontside wheels or the rearside wheels. The double wheel solutions can also be referred to as double-sets.

The at least three wheels 20 are each mounted to the carriage 12 to be pivotable around a vertical pivot axis 26 and to rotate around a horizontal wheel axis 28 (only shown for two wheels in FIG. 1a, but provided for all of the wheels). It is noted that the front side wheels may also be provided to be pivotable around a vertical pivot axis, similar as the axis 26, and to rotate around a horizontal wheel axis, similar to the axis 28. The pivoting movement is indicated with a first circular arrow 27. It is noted that the pivoting movement can take place in both directions. The rotation movement is indicated with a second circular arrow 29. It is noted that the rotation movement can also take place in both directions.

At least two of the at least three wheels 20 are forming rearside wheels $20_{RW}$ mounted in the region of the rear end; and at least one of the at least three wheels 20 is forming a frontside wheel $20_{FW}$ mounted in the region of the front end. At least two of the rearside wheels $20_{RW}$ are independently actively steerable in their orientation around the vertical pivot axis by a pivot actuator (not shown). The at least two of the rearside wheels $20_{RW}$ are configured to be each independently actively drivable around its horizontal axis by a drive actuator (also not shown) to move the mobile base 10 in relation to a floor. The wheel controller 15 is configured to actively steer and drive at least the at least two of the rearside wheels $20_{RW}$ such that the base rotates around a virtual point of rotation VPR that is aligned with the longitudinal center line 17 of the base.

The rearside wheels $20_{RW}$ can also be referred to as backside wheels. The front end can also be referred to as front part or front portion. The rear end can also be referred to as rear part or rear portion.

The wheel controller 15 can also be referred to as drive program or driving module. The wheel controller 15 provides an ease of maneuverability of a mobile C-arm system, for example. The motorized and controlled motion facilitates movement of a C-arm system during procedures inside an operation theater and when transporting in hospital corridors.

In an example, the wheel controller 15 is configured to actively steer the rearside wheels $20_{RW}$ each independently such that the virtual point of rotation VPR is arranged between the first end portion 22 and the opposite second end portion 24 within the base.

In an option, the wheel controller 15 is configured to actively steer the rearside wheels $20_{RW}$ each independently such that the virtual point of rotation VPR is arranged in the center of the mobile base.

In an example, a zero-turning configuration is provided, based on opposite rotations (clockwise and anticlockwise respectively) of the rear left and right wheels. For example, the latter are arranged parallel to each other. In combination with a mobile X-ray system with a C-arm, this provides a rotation of the C-arm around a central axis.

As an example, an imaging system is provided that has a zero turning radius due to the motorized base and independent wheel drive. This allows an in-place C-arm stand rotation.

As an example, the zero turning radius provides an option that considers a heavy system load that may occur with mobile X-ray imaging systems.

In an example, the wheels are mechanically decoupled and a differential drive is implemented for the wheels. A user interface is provided as a steering and control mechanism.

The term "zero turning radius" corresponds to rotating an object around its own axis. This is suitable, for example, for rotating a C-arm stand in small spaces.

Since manual force is not exerted for activating the movement, navigation of the system is facilitated. Using differential wheel drive, the turning radius of the system becomes very small. Hence, the system can be moved easily through small rooms.

In an example, with decoupled wheels and rotating both rear wheels independently, the following motions are provided. To achieve a forward system motion, the right wheel is turning clockwise and the left wheel is also turning clockwise. To achieve a reverse system motion, the right wheel is turning anti-clockwise and the left wheel is also turning anti-clockwise. To achieve an anti-clockwise system motion, the right wheel is turning clockwise and the left wheel is turning anti-clockwise. To achieve a clockwise system motion, the right wheel is turning anti-clockwise and the left wheel is turning clockwise.

In an example, the wheel controller is also configured to actively drive the rearside wheels each independently such that the virtual point of rotation is arranged in the center of the mobile base.

The term "horizontal wheel axis" comprises an axis arranged in an orientation essentially parallel to a floor plane. As an example, the horizontal axis is arranged perpendicular to a vertical or perpendicular axis. In another example, the "horizontal axis" comprises a range of inclination with respect to the horizontal line, such as approximately +/−30°, e.g. approximately up to +/−15° or approximately up to +/−10° or up to +/−5°. The term "vertical pivot axis" comprises an axis arranged in an essentially upright orientation. As an example, the vertical axis is arranged perpendicular to a horizontal floor plane. In another example, the "vertical axis" comprises a range of inclination with respect to the perpendicular line, such as approximately +/−30°, e.g. approximately up to +/−15° or approximately up to +/−10° or up to +/−5°.

In an option (not shown in detail), an inclination of the pivot axis is provided for biasing a certain direction for the wheels in case of no active steering. As an example, the biased position of the pivoting wheels is directed to an arrangement of the wheels for the virtual rotation point below the ISO center. As another example, the biased position of the pivoting wheels is directed to an arrangement of the wheels in which the base can be pushed linearly forward or sideward.

In an option, one actuator is used, and a transmission is provided to steer both rearside wheels, e.g. in a contrary manner or in a synchronized manner.

In an example, the frontside wheels $20_{FW}$ are freely pivotable. In an example, at least one frontside wheel $20_{FW}$ is actively steerable in its orientation around the vertical pivot axis by a pivot actuator.

Thus, multiple rotation points can be achieved or generated, which make it possible to rotate a complete imaging system on the floor around multiple cross/rotation points. This allows larger C-arm panning range compared to e.g. currently ±10°. Linear movements are also still possible in x-, y- or combined directions. In combination with motorized rotation movements, the floor movements are motorized and also the wheel orientations are motorized. This fits with a single user concept where the doctor has control over all movements of the system. In an example, the combination can be used as motorized movements, but it is also still possible to combine this with manual movements. It is also possible to combine this with controlled positions, e.g. automatic position control is provided, which makes it possible e.g. to move with the system between stored position. It is also possible to combine this with scanning movements. Rotations and linear movements are also possible. Movements can be executed parallel to the patient table, perpendicular or combinations of these.

Besides rotation, also linear movements are provided where the rearside wheels are parallel positioned. For example, this can be used for automatic position control (moving between stored positions) or parallel along the patient table, which can also be used for stitching X-ray images. With the combined movements, it is also possible to move the system along a combined trajectory, e.g. linear combined with rotation movements.

In an example, a manual positioning of an imaging system to define a target position is provided and the target position is then stored. The imaging system is moved away, either manually or motorized, to an interim parking position. By activating the drive system, the imaging system can then be moved back to the target position to provide the imaging in the desired position.

In an example, the base is provided for a mobile surgery system. As an option, the system can also be used manually, e.g. during transport to an operating area or for local storage after the procedure has been completed.

In an example, in the case that there is no power available, the base 10 can still be moved manually and then connected with power supply later for further motorized use. In an option, at least one of the rearside wheels $20_{RW}$ is configured to be drivable by the drive actuator.

In an example, the drive actuator is a rearside wheel drive actuator.

In another example, also at least one of the frontside wheels $20_{FW}$ is drivable by a frontside wheel drive actuator.

In an example, the drive actuator comprises one common drive unit or motor, with two transmission devices to independently connect and operate the rearside wheels. The transmission device can also be provided as a gear device.

In another example, the drive actuator comprises a drive for each of the rearside wheels $20_{RW}$.

In an example, the rearside wheels $20_{RW}$ rotates the same directions.

In another example, one of the rearside wheels $20_{RW}$ rotates clockwise and the other one of the rearside wheels $20_{RW}$ rotates counterclockwise, or the opposite directions. This is possible, for example, when each rearside wheel $20_{RW}$ has its drive actuator.

In an example, the pivot actuator is an activatable electro mechanic-actuating element.

In another example, the pivot actuator is a manual steering handle.

In an option, shown in FIGS. 1a and 1b, the wheel controller 15 is configured to actively steer the rearside wheels $20_{RW}$ each independently such that the horizontal wheel axes 28 of the rearside wheels $20_{RW}$ intersect at a cross point 30. The cross point 30 is aligned with the longitudinal center line 17 and forms the virtual point of rotation VPR of the mobile base. The virtual point of rotation VPR is arranged in front of the at least one front wheel, or rear of a virtual connection line of the two rear wheels. The virtual point of rotation VPR can also be referred to as flexible point of rotation or virtual rotation point, VRP.

It is noted that to arrange the virtual point of rotation VPR in front of the at least one front wheel, or rear of a virtual connection line of the two rear wheels, is provided as an option.

In an example, the wheel controller 15 is also configured to actively drive the rearside wheels each independently such that the horizontal wheel axes of the rearside wheels intersect at a cross point. The cross point is aligned with the longitudinal center line and forms the virtual point of rotation VPR of the mobile base.

In an option, the wheel controller is configured to steer the rearside wheels $20_{RW}$ each independently to drive along a part of a circular arc 32 with a center point of rotation. The center point of rotation forms the virtual point of rotation VPR of the mobile base 10. The virtual point of rotation VPR of the mobile base 10 is also referred to as virtual rotation axis for the mobile base.

FIGS. 1a and 1b show an example where the rearside wheels $20_{RW}$ are arrangeable along a circular line (i.e. the circular arc 32) that is concave when viewed from the frontside wheels $20_{FW}$. The virtual point of rotation VPR is thus arranged on a side of the rearside wheels $20_{RW}$ that is facing towards an object during imaging. It is noted that the movement is possible in both directions along the circular arc 32.

Figure 2A:
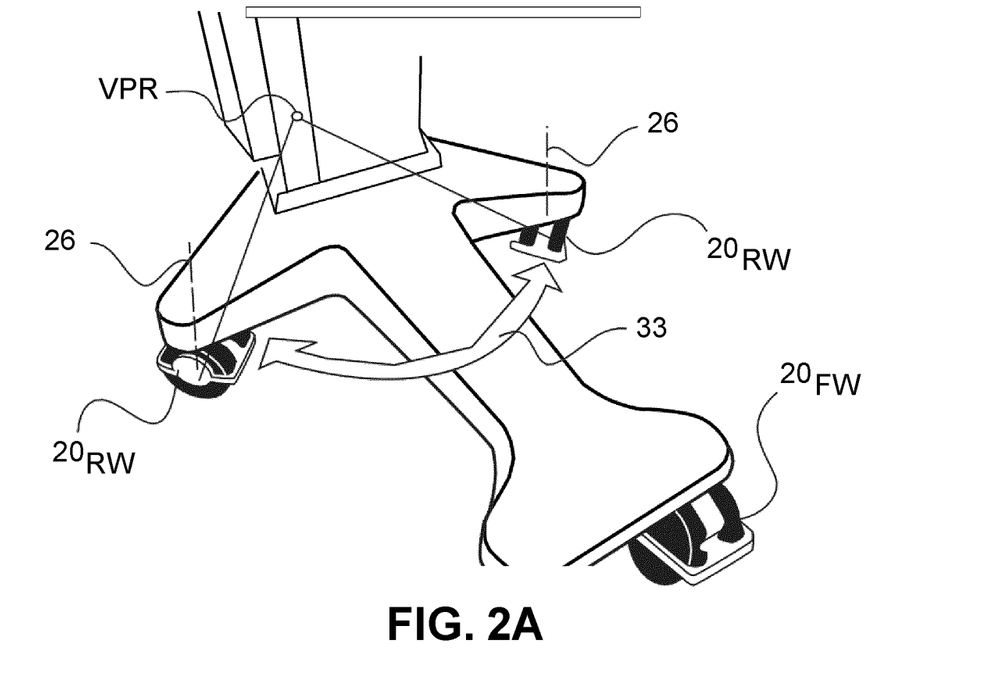
FIGS. 2a and 2b show the example of the base of FIGS. 1a and 1b with a second wheel arrangement in two perspective views.
Figure 2B:
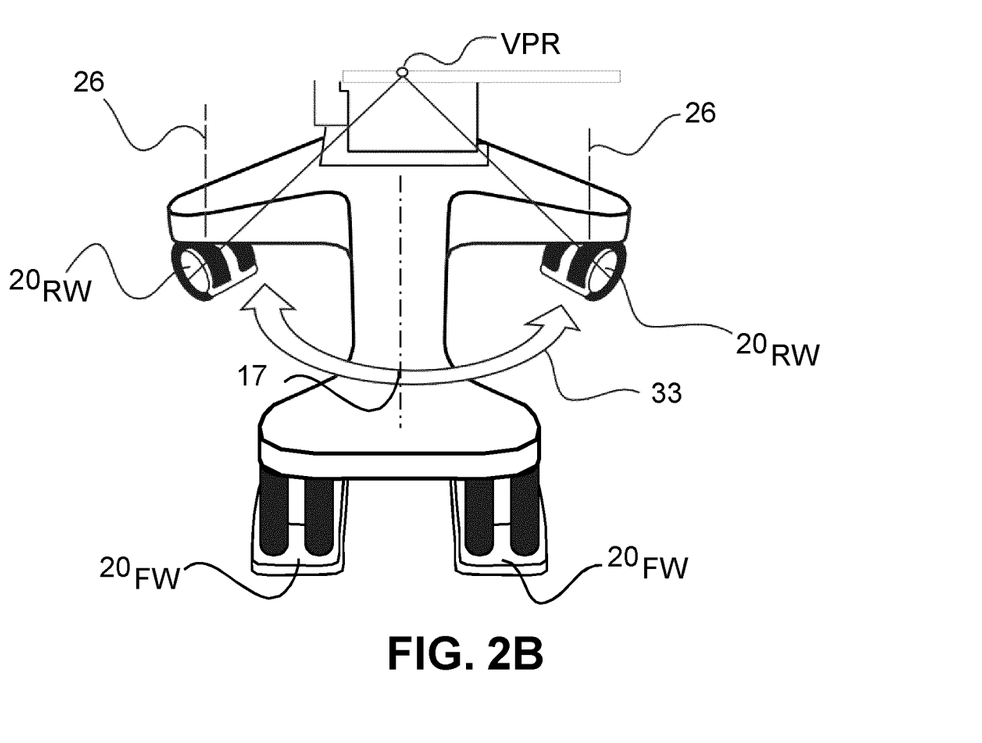

FIGS. 2a and 2b show an example where the rearside wheels $20_{RW}$ are arrangeable along a circular line (i.e. a circular arc 33) that is convex when viewed from the frontside wheels $20_{FW}$. The virtual point of rotation VPR is thus arranged on a side of the rearside wheels $20_{RW}$ that is facing away from an object during imaging. It is noted that the movement is possible in both directions along the circular arc 33.

As an option, it is provided that the also at least one frontside wheel $20_{FW}$ is independently actively steerable in its orientation around the vertical pivot axis and the wheel controller 15 is configured to actively steer the at least one frontside wheel $20_{FW}$.

In an example, the at least one frontside wheel $20_{FW}$ is independently actively steerable by a frontside wheel pivot actuator (not shown in detail, e.g. enclosed in the housing or cover).

In an example, the same pivot actuator as for the rearside wheels is used for the front side wheels. In an example, a frontside wheel pivot actuator is provided.

As a further option, it is provided that the at least one frontside wheel is independently actively drivable around its horizontal axis by a drive actuator (not shown in detail, e.g. enclosed in the housing or cover), and the wheel controller 15 is configured to actively drive the at least one frontside wheel.

In an example, the at least one frontside wheel is independently actively drivable by a frontside wheel drive actuator (not shown in detail, e.g. enclosed in the housing or cover).

In an example, the same drive actuator as for the rearside wheels is used for the front side wheels. In an example, a frontside wheel drive actuator is provided (not shown in detail, e.g. enclosed in the housing or cover).

In an example, the frontside wheels $20_{FW}$ are independently steerable by a pivot actuator (not shown in detail, e.g. enclosed in the housing or cover). The pivot actuator may be provided as a separate pivot actuator. In an option, the same pivot actuator is used as for the rearside wheels, but with a separate transmission device, or gear device, connecting the frontside wheels to the pivot actuator.

In an example, the wheel controller 15 comprises a program to execute at least one predefined rotation of the group of: i) rotation of the base around the virtual point of rotation being arranged in the center of the base; ii) rotation of the base around the virtual point of rotation being arranged in front of the front end of the base; and iii) rotation of the base around the virtual point of rotation being arranged beyond the rear end of the base.

In an example, the controller is provided as a wireless controller, for example arranged with a user interface to easily control the motions. The user interface may be provided as a joystick or as a touch sensitive graphic display showing an illustration of the base to activate the rotation of the base.

In an example, the user interface comprises a virtual or actual button dedicated to select one or the other of each rotation. If virtual, this button may be selectable, for example by a button for "forward rotation", "rear rotation", "central rotation" together with the direction of rotation (clockwise—anticlockwise) for each rotation.

In FIGS. 1a/1b and 2a/2b, different movement directions are shown depending on the backside wheel orientations. A first situation shows that the flexible rotation point is in the front; e.g. this could be in the center of the image chain. A second situation shows the flexible rotation point at the back; e.g. this could be the center of the panning rotation.

Figure 3A:
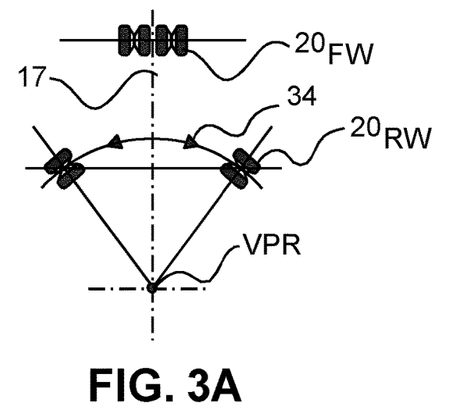
FIGS. 3a, 3b, 3c, 3d and 3e schematically show different wheel arrangements of the base of FIGS. 1a and 1b.

FIG. 3a shows the movement of the rearside wheels $20_{RW}$ along a first curve 34 in two directions, as indicated with a double arrow.

Figure 3B:
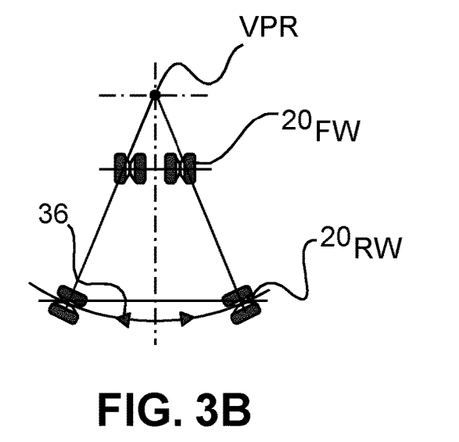

FIG. 3b shows the movement of the rearside wheels $20_{RW}$ along a second curve 36 in two directions, as indicated with a double arrow.

Figure 3C:
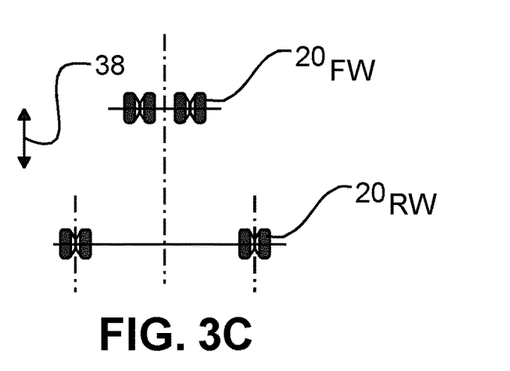

FIG. 3c shows the movement of the rearside wheels $20_{RW}$ and the frontside wheels $20_{FW}$ in a first parallel direction 38 in two directions, as indicated with a double arrow.

Figure 3D:
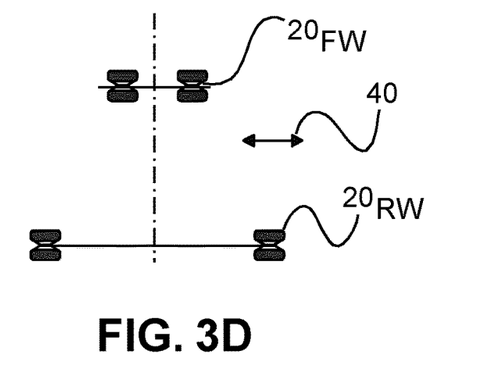

FIG. 3d shows the movement of the rearside wheels $20_{RW}$ and the frontside wheels $20_{FW}$ in a second parallel direction 40 in two directions, as indicated with a double arrow.

Figure 3E:
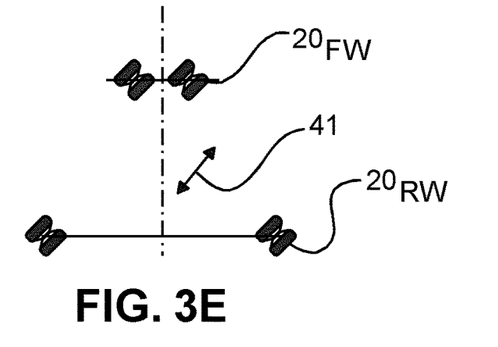

FIG. 3e shows the movement of the rearside wheels $20_{RW}$ and the frontside wheels $20_{FW}$ in an angled direction, as indicated with a double arrow 41.

Figure 3F:
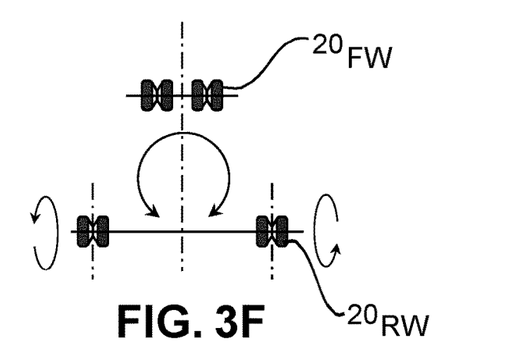
FIG. 3f shows a wheel arrangement of the base for a movement around a central axis.

FIG. 3f shows the movement around a central axis.

Figure 4:
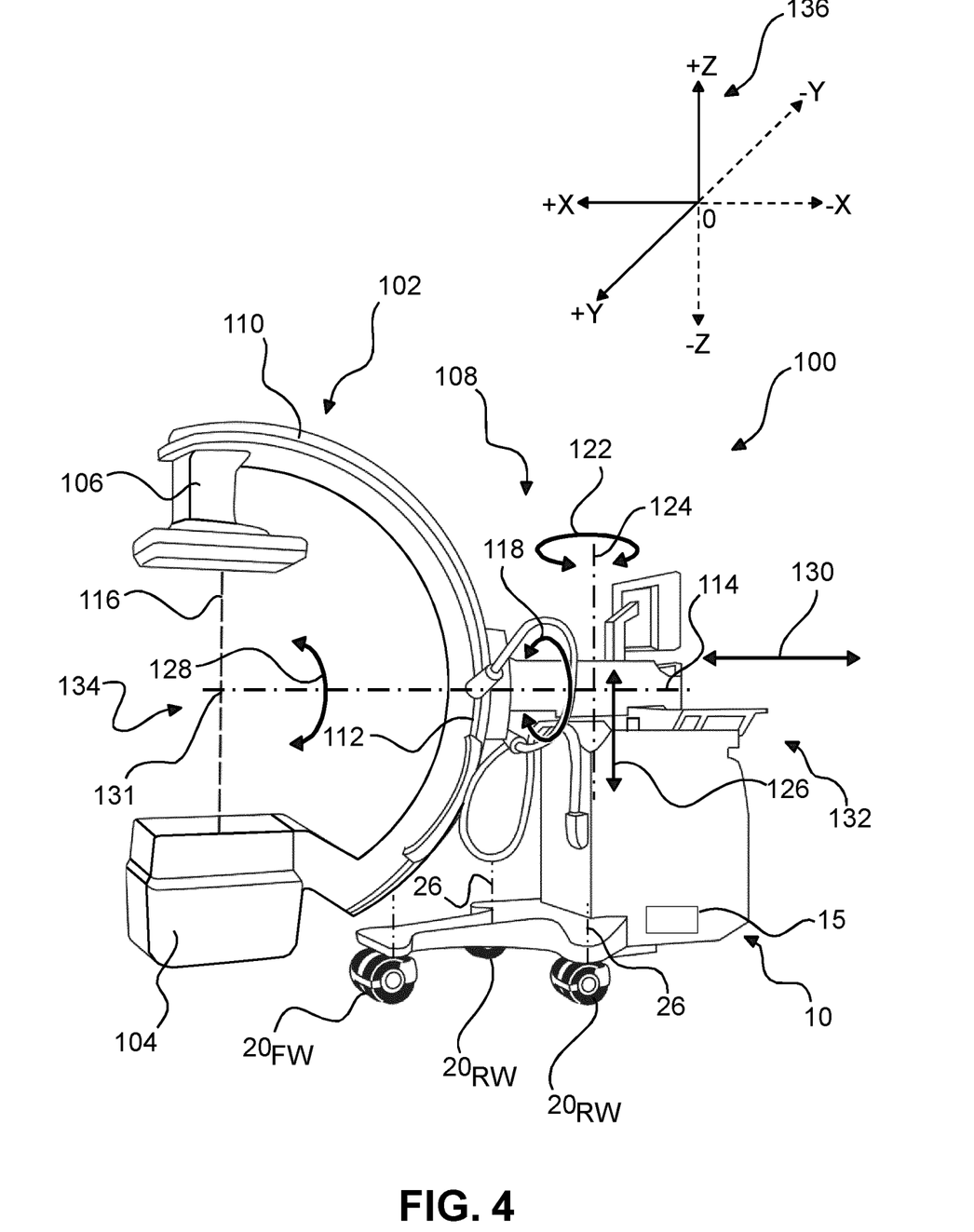
FIG. 4 shows an example of an X-ray imaging system with the base of FIGS. 1a and 1b.

FIG. 4 shows a mobile X-ray imaging system 100. The imaging system 100 can also be referred to as Mobile Surgery system. The system comprises an example of the base 10 according to one of the preceding examples. Further, an X-ray imaging device 102 is provided with an X-ray source 104 and an X-ray detector 106. The X-ray imaging device 102 comprises a support structure 108. At least the X-ray source 104 is mounted to the support structure 108. The support structure 108 is movably mounted to the mounting structure 14 of the base 10. In an example, also the X-ray detector 106 is mounted to the support structure 108.

As an option, the support structure 108 comprises a C-arm 110, as shown, and the X-ray source 104 and the X-ray detector 106 are mounted to opposite ends of the C-arm 110. An object, such as a subject arranged on a subject support, can be arranged between the X-ray source 104 and the X-ray detector 106 (not further shown) for X-ray imaging.

Further, the C-arm 110 is slidably hold by a sleeve-like mount 112, which is rotatable around a horizontal axis of rotation 114. The horizontal axis of rotation 114 and a centerline 116 between the X-ray source and the X-ray detector are crossing each other at a point of intersection 131. This is also referred to as ISO center. The sleeve-like mount 112 is also rotatable around a vertical axis of rotation (see axis 124 below). The X-ray imaging C-arm 110 is also referred to as X-ray imaging C-arc. The sleeve-like mount 112 is movably hold by a connecting portion of the support structure 108, which connection portion may be provided to achieve further movements in relation to the mounting structure 14 of the base. The following movement possibilities may be provided:

- a propeller-like swiveling 118 of the C-arm around the horizontal axis 114, which is also referred to as C-arm rotation;
- a horizontal rotation 122 around a vertical axis 124, which is also referred to as C-arm panning rotation;
- a height adjustment 126, which is also referred to as height movement;
- a sliding motion within the sleeve resulting in a rotation 128 of the C-arm, which is also referred to as C-arm angulation; and
- a horizontal movement 130, which is also referred to as C-arm horizontal movement.

In view of the designated use, the right side in the figure is referred to as back side 132, i.e. away from an object, and the left side is referred to as front side 134, i.e. towards an object.

A three-axis coordinate system 136 indicates the different axes of the imaging system 100. An x-axis in a horizontal manner is assigned to the front-rear direction; a y-axis in a horizontal manner is assigned to the left-right direction; and a z-axis in a vertical manner is assigned to the down-up direction.

As an option, the virtual point of rotation VPR of the mobile base 10 and the point of intersection 131 are alignable in a vertical manner.

In an option, the point of intersection 131 forms an ISO-center of the X-ray imaging device 102.

In another option, the virtual point of rotation VPR of the mobile base 10 and the vertical axis of rotation are alignable in a vertical manner.

In an example, the two alignment options are both provided. This allows an increased range for panning the X-ray source in relation to an object. The movement range is enlarged. Also, this makes it possible to use a smaller carriage, since the center of gravity stays in one line and doesn't move sideward. As a further result, the center of gravity also does not move with the panning movement anymore.

In an example, the C-arm is provided on a frontside of the mounting structure, i.e. facing towards an object during imaging.

In addition, the C-arm 110 is adjustable in height. For example, the support structure (or the mounting structure) comprises a height movement device.

As a further option of the base, the wheel controller 15 comprises a user interface 19 to trigger a rotation of the base around the virtual point of rotation being aligned with the longitudinal center line of the base. It is noted that the interface 19 is shown in a few figures. However, in some examples, the interface 19 is also provided for the examples of the other figures.

As an option, the user interface 19 is provided as at least one of the group of: a joy stick, a steering wheel or remote steering console to actively control the movement, a remote control handle enabling and controlling the drive and steer mechanism, and a gesture recognizer to allow gesture control of the movement of the base.

In an example, different steering mechanisms are provided as user interface to realize intended motion. Examples are joy sticks, handles (which contain to enable and to control the mechanism) and steering wheels.

For example, a joystick is be used as the user interface 19 to enable and control movement of mobile C-arm system to move it forward/backward or to rotate clockwise/anti-clockwise. The controlled movements are achieved by microcontroller based motor driver for motorized wheels.

It is noted that although the user interface 19 is described in relation with an X-ray imaging system, also only the base is provided supplemented by the user interface, but without the imaging system.

In a further option, also shown in the context of the X-ray imaging system, but not limited thereto, a collision control 21 is provided that is configured to detect obstacles in a current rotational pathway. The wheel controller 15 is configured to adapt the wheels in their orientation around their vertical axes such that an adjusted pathway is provided avoiding a collision with the detected obstacles.

In an example, the collision control 21 comprises a sensor arrangement 23 provided on the base and/or the imaging system to provide the spatial situation in the vicinity.

This provided the possibility e.g. to prevent the rotation in case an obstacle is detected and angularly localized, such as in the coordinate system defined by the axis of the selected rotation of the base. The sensors are, for example, mounted to the base or the C-arm. The sensors are configured to scan at least a part the path of the required rotation. They can scan the path from start to end, for example, or just the next part. In case the path is fully predetermined, the rotation can be prevented before rotation. If the angle of rotation is determined manually, the rotation may be stopped as soon as the angular position of an obstacle is located in an angular range, starting from the angle of rotation of the base, and lower than a threshold angular range. As an option, a switch in the operation of use can be provided, and the base may switch from the rear or forward rotation to the central rotation, if such obstacle is detected. It can then be checked again if the adapted path is free of obstacles or not for this central rotation. It may also be provided to switch from central rotation to rear or forward rotation or from rear to rotation. The switching may be provided for cases where the system is in a displacement mode and not in a scanning mode.

Figure 5A:
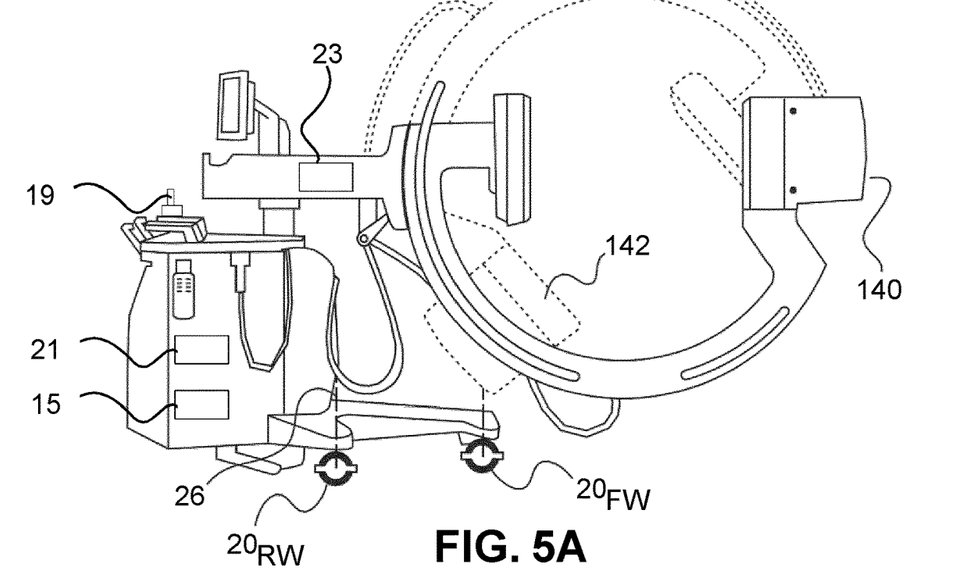
FIGS. 5a and 5b show the example of FIG. 4 in different positions shown in an overlaid manner.

It is noted that the collision control 21 is shown in a FIG. 5A. However, in some examples, the interface 19 is also provided for the examples of the other figures, e.g. FIG. 4 or FIGS. 1A, 1B, 2A, 2B, 5B, 6A, 6B and 7.

The term "central rotation" relates to a rotation around the virtual point of interest being arranged within the base, e.g. in the middle of the base. The term "rear rotation" relates to a rotation when the virtual point of interest is arranged behind the base. The term "forward rotation" relates to a rotation around the virtual point of interest being arranged in front of the base.

Figure 5B:
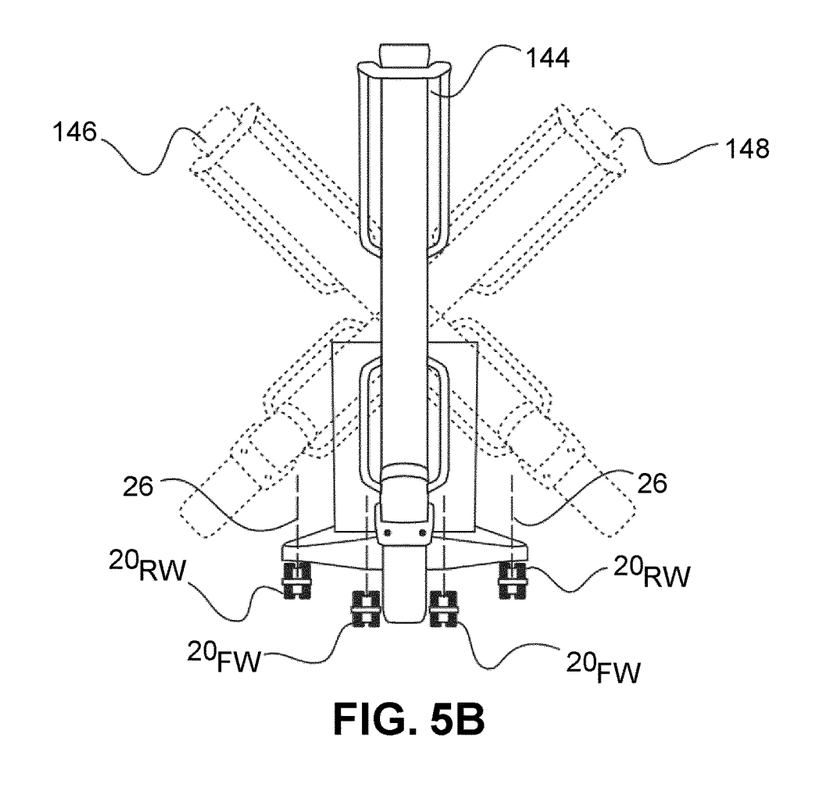

FIGS. 5a and 5b show the example of FIG. 4 in different positions shown in an overlaid manner.

FIG. 5a shows a side view of the C-arm in a first extreme or end position 140 of the C-arm angulation and also in a second extreme or end position 142 of the C-arm angulation.

FIG. 5b shows a front view of the C-arm in a middle or upright position 144 and in a first extreme or end position 146 of the C-arm angulation and a second extreme or end position 148 of the rotation, or propeller-like rotation.

Figure 6A:
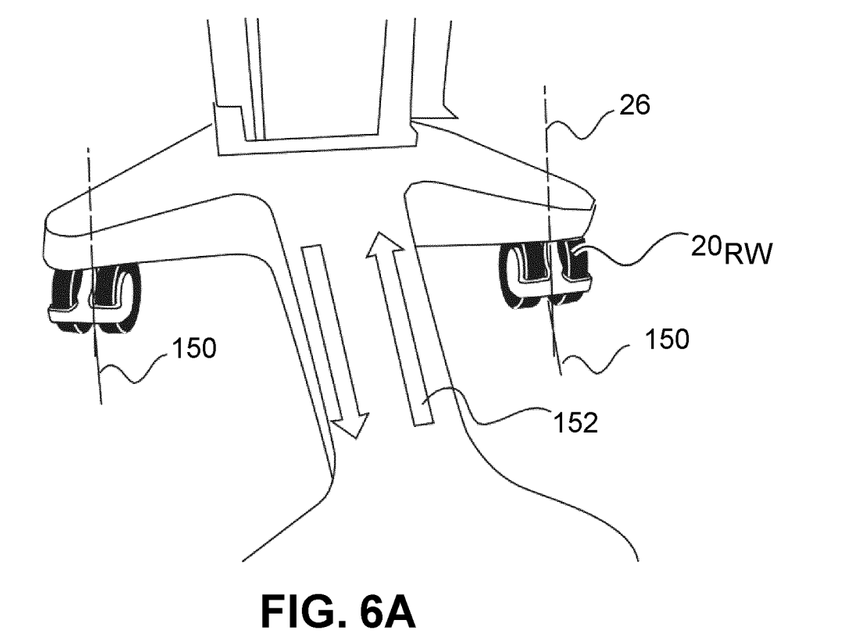
FIGS. 6a and 6b show the example of the base of FIGS. 1a and 1b with two further wheel arrangements.
Figure 6B:
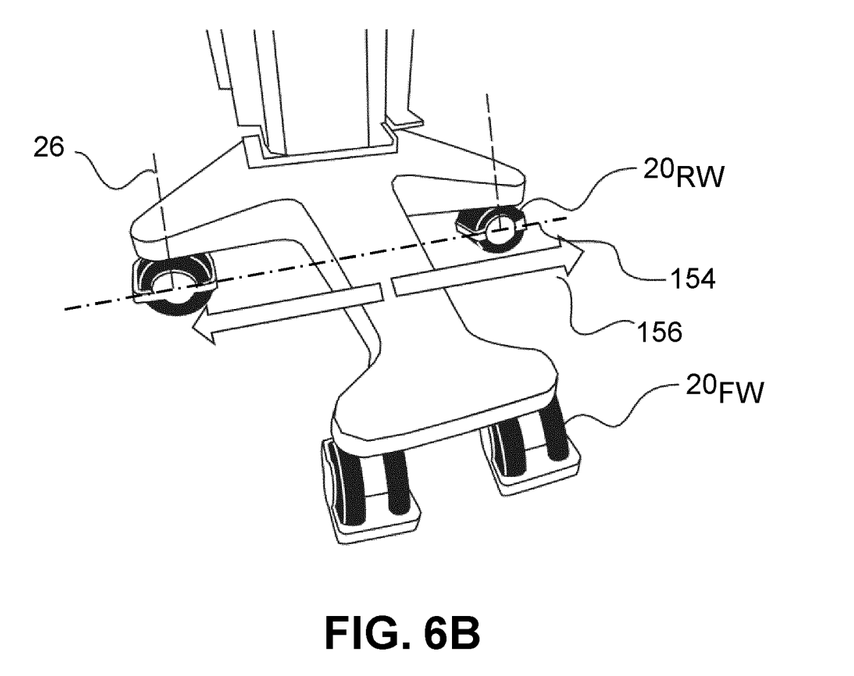

FIGS. 6a and 6b show the example of the base 10 of FIGS. 1a and 1b with two further wheel arrangements. FIG. 6a shows the rearside wheels $20_{RW}$ with their direction of rotation being in a first parallel alignment 150, resulting in possible linear movement in two directions 152. FIG. 6b shows the rearside wheels $20_{RW}$ with their direction of rotation being in a second parallel alignment 154, resulting in possible linear movement in two further directions 156. When combining X- and Y-orientation of the wheels, an inclined (referred to the horizontal axes x and y) linear movement is also possible (see also FIG. 3e).

In FIGS. 6a and 6b, a third and fourth situation show the two linear movements where the backside wheels are parallel positioned; e.g. this can be used for automatic position control (moving between stored positions) or parallel along the patient table. The fourth situation can also be used for stitching X-ray images.

Figure 7:
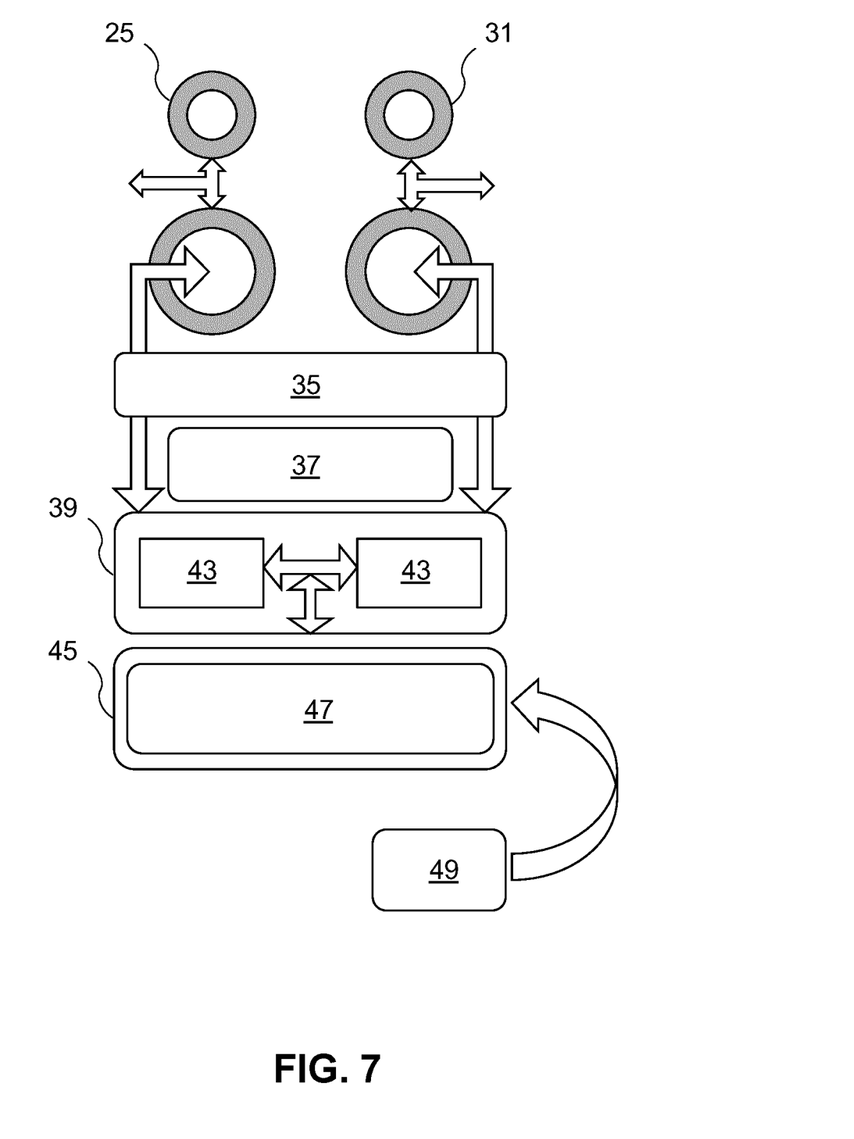
FIG. 7 shows another example of a base with a steerable and drivable wheel arrangement.

FIG. 7 shows another example of the base with a steerable and drivable wheel arrangement with left wheels 25 and right wheels 31. A mechanical coupling 35 is provided that is connected to a power supply 37. A motor frame 39 indicates two motors 43 and a controller 45 is provided as the wheel controller 47, also comprising a motor driving circuitry. As a user interface, a joystick 49 is provided.

Figure 8:
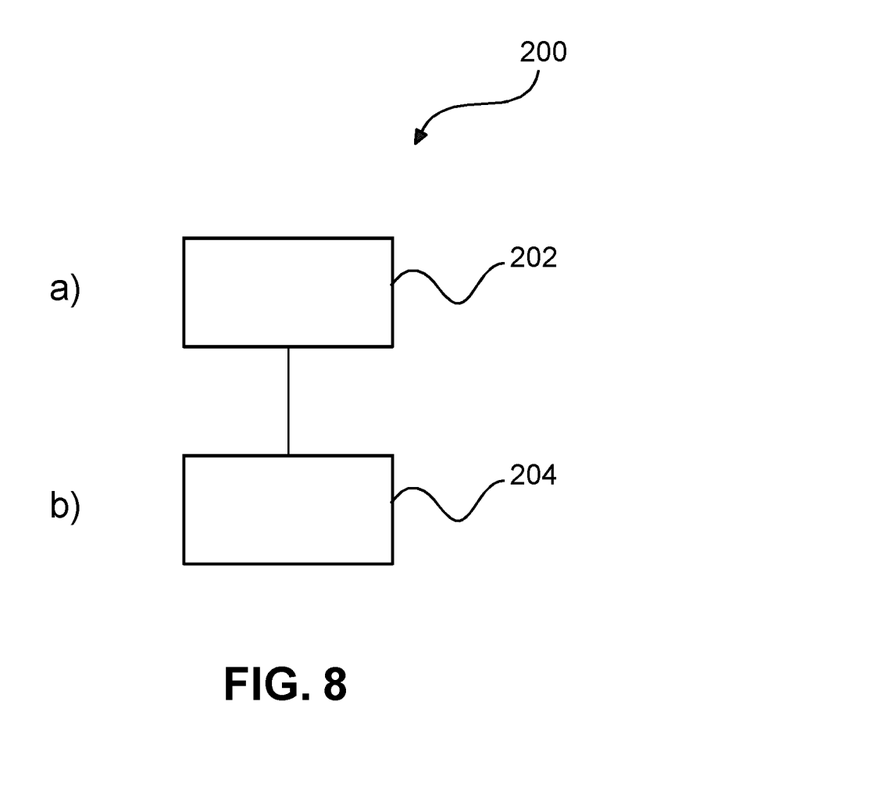
FIG. 8 shows an example of steps of a method for moving a base of a mobile X-ray imaging system.

FIG. 8 shows an example of a method 200 for moving a base of one of the examples above or the base of a mobile X-ray imaging system of one of the examples above. The method 200 comprises the following steps:

In a first step 202, the controller is independently actively steering at least the at least two of the rearside wheels.

In a second step 204, the controller is actively driving (204) at least the at least two of the rearside wheels.
The steering and driving causes the base rotating around a virtual point of rotation that is aligned with the longitudinal center line of the base.

In an example, the first and second step take place at the same time. In another example, the first and second step take place in an overlapping and/or displaced manner.

In another example, a method for moving a base of a mobile X-ray imaging system is provided. The method 200 comprises the following steps:

In a first step, also referred to as step a), independently actively steering of rearside wheels is provided of a wheel arrangement of at least three wheels mounted to the carriage in their orientation around a vertical pivot axis by a pivot actuator. The wheels are each mounted to the carriage to be pivotable around a vertical pivot axis; and In a second step, also referred to as step b), actively driving at least one of the wheels by a drive actuator is provided to move the mobile base in relation to a floor. The at least three wheels are each mounted to the carriage to rotate around a horizontal wheel axis.

The wheels are mounted to a carriage to which a mounting structure is mounted, which mounting structure is configured to movably hold an X-ray imaging device.

The carriage comprises a first end portion and an opposite second end portion; the first end portion being configured as a front end arrangeable closer to an object during X-ray imaging, and the second end portion being configured as a rear end arrangeable away from an object during X-ray imaging. Further, at least two of the at least three wheels are forming rearside wheels mounted in the region of the rear end; and at least one of the at least three wheels is forming a frontside wheel mounted in the region of the front end.

The two steps may be provided in parallel.

In an option, not further shown in detail, in step b), at least one of the rearside wheels is driven by the drive actuator.

For example, images can be made with a parallel movement or a rotation similar like the panning rotation; in an example, this is combined with a horizontal movement to minimize the unwanted offset direction. With automatic position, it is possible to move from or towards the patient to make space available around the patient for the operator and or doctor, and to move towards the patient to make X-ray images at the same stored position. In an additional option, the base 10 for a mobile X-ray imaging system is combined with a navigation system that controls or guides the moving directions.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit or be distributed over more than one computer units, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

Aspects of the invention may be implemented in a computer program product, which may be a collection of computer program instructions stored on a computer readable storage device which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

As discussed above, the processing unit, for instance a controller implements the control method. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A base for a mobile X-ray imaging system, the base comprising:
    a carriage comprising a first end portion and an opposite second end portion, the first end portion configured as a front end arrangeable closer to an object during X-ray imaging than the opposite second end portion configured as a rear end, the first end portion and the opposite second end portion arranged along a longitudinal center line of the base;
    a mounting structure mounted to the carriage, the mounting structure configured to movably hold an X-ray imaging device;
    a wheel base with a wheel arrangement of at least three wheels, each of the at least three wheels mounted to the carriage to be pivotable around a vertical pivot axis and rotatable around a horizontal wheel axis,
    wherein at least two of the at least three wheels forming at least two rearside wheels mounted in a region of the rear end and at least one of the at least three wheels forms a frontside wheel mounted in a region of the front end, each of the at least two rearside wheels independently actively steerable in an orientation around the vertical pivot axis and drivable around the horizontal wheel axis to move the base in relation to a floor;
    a pivot actuator configured to independently actively steer each of the at least two rearside wheels to be pivoted in the orientation around the vertical pivot axis;
    a drive actuator configured to independently actively drive each of the at least two rearside wheels to be rotated around the horizontal wheel axis; and
    a wheel controller configured to control the pivot actuator to independently actively steer each of the at least two rearside wheels to be pivoted in the orientation around the vertical pivot axis and control the drive actuator to independently actively drive each of the at least two of the rearside wheels to be rotated around the horizontal axis to rotate the base around a virtual point of rotation that is aligned with the longitudinal center line of the base.

2. The base according to claim 1, wherein the wheel controller is configured to:
    actively steer each of the rearside wheels independently such that the virtual point of rotation is arranged between the first end portion and the opposite second end portion within the base;
    actively steer each of the rearside wheels independently such that the virtual point of rotation is arranged in a center of the mobile base.

3. The base according to claim 1, wherein:
    the wheel controller is configured to actively steer each of the rearside wheels independently such that the horizontal wheel axis of the respective rearside wheel intersects at a cross point;
    the cross point is aligned with the longitudinal center line and forms the virtual point of rotation of the base; and
    the virtual point of rotation is arranged in front of the at least one frontside wheel or rear of a virtual connection line of the at least two rearside wheels.

4. The base according to claim 1, wherein:
    the at least one frontside wheel is independently actively steerable in the orientation around the vertical pivot axis; and
    the wheel controller is configured to control the pivot actuator to actively steer the at least one frontside wheel.

5. The base according to claim 1, wherein:
    the at least one frontside wheel is independently actively drivable around the horizontal wheel axis of the at least one frontside wheel; and
    the wheel controller is configured to control the drive actuator to actively drive the at least one frontside wheel.

6. The base according to claim 1, wherein:
    the wheel controller comprises a user interface to trigger a rotation of the base around the virtual point of rotation being aligned with the longitudinal center line of the base; and the user interface is provided as at least one of:
- a joy stick, a steering wheel or a remote steering console to actively control the movement;
- remote control handle, enabling and controlling the drive and steer mechanism; or
- gesture recognizer to allow gesture control of the movement of the base.

7. The base according to claim 1, wherein the wheel controller is configured to execute at least one predefined rotation of:
- i) rotation of the base around the virtual point of rotation being arranged in the center of the base;
- ii) rotation of the base around the virtual point of rotation being arranged in front of the front end of the base; and
- iii) rotation of the base around the virtual point of rotation being arranged beyond the rear end of the base.

8. A mobile X-ray imaging system, comprising:
the base according to claim 1; and
an X-ray imaging device with an X-ray source and an X-ray detector, the X-ray imaging device comprising a support structure and the X-ray source is mounted to the support structure,
wherein the support structure is movably mounted to the mounting structure of the base.

9. The X-ray imaging system according to claim 8, wherein:
the support structure comprises a C-arm, and the X-ray source and the X-ray detector are mounted to opposite ends of the C-arm;
the C-arm is slidably hold by a sleeve-like mount, which is rotatable around a horizontal axis of rotation;
the horizontal axis of rotation and a centerline between the X-ray source and the X-ray detector are crossing each other at a point of intersection; and
the sleeve-like mount is rotatable around a vertical axis of rotation.

10. The X-ray imaging system according to claim 9, wherein the virtual point of rotation of the base and the point of intersection are alignable in a vertical manner.

11. The X-ray imaging system according to claim 8, further comprising a collision control that is configured to detect obstacles in a current rotational pathway,
wherein the wheel controller is configured to adapt each wheel the at least three wheels in the orientation around the vertical axis of the wheel such that an adjusted pathway is provided to avoid a collision with the detected obstacles.

12. A method for moving a base for a mobile X-ray imaging system, the method comprising:
controlling movement of the base for the mobile X-ray imaging system, wherein the base comprises:
a carriage comprising a first end portion and an opposite second end portion, the first end portion configured as a front end arrangeable closer to an object during X-ray imaging than the opposite second end portion configured as a rear end, the first end portion and the opposite second end portion arranged along a longitudinal center line of the base,
a mounting structure mounted to the carriage, the mounting structure configured to movably hold an X-ray imaging device, and
a wheel base with a wheel arrangement of at least three wheels mounted to the carriage, each of the at least three wheels mounted to the carriage to be pivotable around a vertical pivot axis and to rotate around a horizontal wheel axis, wherein at least two of the at least three wheels form rearside wheels mounted in a region of the rear end and at least one of the at least three wheels forms a frontside wheel mounted in a region of the front end, and wherein the rearside wheels include at least two rearside wheels that are independently actively steerable in an orientation around the vertical pivot axis by a pivot actuator and drivable around a horizontal axis by a drive actuator to move the base in relation to a floor; and
rotating the base around a virtual point of rotation that is aligned with the longitudinal center line of the base by controlling the pivot actuator to independently actively steer each of the at least two rearside wheels to be pivoted in the orientation around the vertical pivot axis and controlling the drive actuator to independently actively drive each of the at least two rearside wheels to be rotated around the horizontal axis.

13. The method according to claim 12, wherein:
the each of the rearside wheels are independently steered such that the horizontal wheel axis of the respective rearside wheel intersects at a cross point that is aligned with the longitudinal center line and forms the virtual point of rotation of the base; and
the virtual point of rotation is arranged in front of the at least one frontside wheel or rear of a virtual connection line of the at least two rearside wheels.

14. The method according to claim 12, wherein:
the at least one frontside wheel is independently actively steerable in the orientation around the vertical pivot axis and independently actively drivable around the horizontal wheel axis of the at least one frontside wheel; and
the method further comprises controlling the pivot actuator to actively steer the at least one frontside wheel and controlling the drive actuator to actively drive the at least one frontside wheel.

15. The method according to claim 12, wherein rotating the base around the virtual point of rotation comprises at least one predefined actions of:
- i) rotating the base around the virtual point of rotation being arranged in the center of the base;
- ii) rotating the base around the virtual point of rotation being arranged in front of the front end of the base; and
- iii) rotating the base around the virtual point of rotation being arranged beyond the rear end of the base.

16. A non-transitory computer-readable storage medium having stored a computer program comprising instructions, which, when executed by a processor, cause the processor to:
control movement of a base for a mobile X-ray imaging system, wherein the base comprises:
a carriage comprising a first end portion and an opposite second end portion, the first end portion configured as a front end arrangeable closer to an object during X-ray imaging than the opposite second end portion configured as a rear end, the first end portion and the opposite second end portion arranged along a longitudinal center line of the base,
a mounting structure mounted to the carriage, the mounting structure configured to movably hold an X-ray imaging device, and
a wheel base with a wheel arrangement of at least three wheels mounted to the carriage, each of the at least three wheels mounted to the carriage to be pivotable around a vertical pivot axis and to rotate around a horizontal wheel axis, wherein at least two of the at least three wheels form rearside wheels mounted in a region of the rear end and at least one of the at least three wheels forms a frontside wheel mounted in a region of the front end, and wherein the rearside wheels include at least two rearside wheels that are independently actively steerable in an orientation around the vertical pivot axis by a pivot actuator and drivable around a horizontal axis by a drive actuator to move the base in relation to a floor; and control the pivot actuator to independently actively steer each of the at least two rearside wheels to be pivoted in the orientation around the vertical pivot axis and control the drive actuator to independently actively drive each of the at least two rearside wheels to be rotated around the horizontal axis to rotate the base around a virtual point of rotation that is aligned with the longitudinal center line of the base.

17. The non-transitory computer-readable storage medium according to claim 16, wherein:

the each of the rearside wheels are independently steered such that the horizontal wheel axis of the respective rearside wheel intersects at a cross point that is aligned with the longitudinal center line and forms the virtual point of rotation of the base; and the virtual point of rotation is arranged in front of the at least one frontside wheel or rear of a virtual connection line of the at least two rearside wheels.

18. The non-transitory computer-readable storage medium according to claim 16, wherein:

the at least one frontside wheel is independently actively steerable in the orientation around the vertical pivot axis and independently actively drivable around the horizontal wheel axis of the at least one frontside wheel; and the instructions, when executed by the processor, further cause the processor to control the pivot actuator to actively steer the at least one frontside wheel and control the drive actuator to actively drive the at least one frontside wheel.

19. The non-transitory computer-readable storage medium according to claim 16, wherein, to rotate the base around the virtual point of rotation, the instruction, when executed by the processor, further cause the processor to at least one of:

i) rotate the base around the virtual point of rotation being arranged in the center of the base;

ii) rotate the base around the virtual point of rotation being arranged in front of the front end of the base; and iii) rotate the base around the virtual point of rotation being arranged beyond the rear end of the base.

\* \* \* \* \*